United States Patent [19]
Andermann

[11] Patent Number: 5,516,765
[45] Date of Patent: May 14, 1996

[54] THERAPEUTIC METHOD FOR THE TREATMENT OR PREVENTION OF SNORING

[76] Inventor: Guy Andermann, 2, Rond Point de l'Esplanade, F, 67000 Strasbourg, France

[21] Appl. No.: 359,342

[22] Filed: Dec. 19, 1994

Related U.S. Application Data

[63] Continuation of Ser. No. 868,473, Apr. 14, 1992, abandoned, which is a continuation of Ser. No. 505,933, Apr. 6, 1990, abandoned.

[30] Foreign Application Priority Data

Apr. 12, 1989 [FR] France ................... 89 05029

[51] Int. Cl.$^6$ ........................................ A61K 31/70
[52] U.S. Cl. ............................. 514/54; 536/55.1
[58] Field of Search ................. 514/54; 536/54, 536/55.1

[56] References Cited

U.S. PATENT DOCUMENTS 4,965,253  10/1990  Goldberg et al. ................ 514/54

OTHER PUBLICATIONS

Miyake et al. Chemical Abstracts, vol. 108 (1988) No. 68975a.

Adam et al, Chemical Abstracts, vol. 108 (1988) No. 118871m.

Nakamura et al. Chemical Abstracts, vol. 113 (1990) No. 12179e.

*Primary Examiner*—Elli Peselev
*Attorney, Agent, or Firm*—Rosenthal & Putterman

[57] ABSTRACT

This new solution according to the invention, contains mucopolysaccharides of the glycosaminoglycane type as principle active agent, and more precisely sodic chondroitin sulphate. The excipient of this composition contains at least one mercury preserving agent, one substance with isotonic properties, and a phosphate buffer. The principle active agent may be combined with plant or mineral compounds, or with homeopathic or allopathic concentrations which synergise its therapeutic activities.

10 Claims, No Drawings

THERAPEUTIC METHOD FOR THE TREATMENT OR PREVENTION OF SNORING

This is a continuation of application Ser. No. 07/868,473 filed Apr. 14, 1992, now abandoned, which in turn is a continuation of U.S. patent application No. 07/505,933, filed Apr. 6, 1990, now abandoned.

FIELD OF THE INVENTION

This invention concerns the field of solutions for nasal instillations, and more precisely a nasal solution for the treatment or prevention of snoring, or the symptoms of snoring.

BACKGROUND OF THE INVENTION

It is well known that people who snore are a source of disturbance and annoyance to those around them. In fact, snoring is a sound which comes from abnormal vibrations of the soft palate. Moreover, very often the snorer suffers from a blockage of the nasal fossae, which worsens the ailment.

It will be noted that a difference must be made between ordinary snorers and chronic snorers, who may be suffering from a serious ailment, namely, sleep apnoea syndrome (SAS).

The treatments which are currently in use consist of surgery (uvula-palatal-pharynogoplastic surgery), or of electronic signals which are applied to the brain and send out messages to the snorer which wake him and force him to change position. Other treatments such as acupuncture or medicinal treatments which consist in instilling nasal drops have also been used. Vasoconstrictors, which decongest the nasal mucus (U.S. Pat. No. 2,989,437) or surface-active agents which sometimes contain glycerine, such as those disclosed in U.S. Pat. No. 4,556,557, are also known. The surface-active agents may take the form of cationic, anionic or non-toxic surfactants, such as those used in commercialized products such as Phonarex® or Ronfulux®, which are available in some European countries.

The above mentioned products attempt to hydrate the nasal mucus, but due to the short period of contact of these compounds with the mucus, it results in products that are not very efficient, except in the cases whereby they are applied repeatedly throughout the night. Moreover, some of these products are likely to cause nasal hemorrhages which may in certain cases be serious if these products are misused. The vasoconstrictors of the naphazoline, tetryzoline or xylometzaline types, or all those derived from phenylpropanolamine create a certain dependency and secondary effects whose symptoms take the form of a type of drug addiction.

These surface-active products have largely been abandoned as they do not have the characteristics required to remain in contact with the tissues of the nasal mucus for a sufficiently long period.

In view of the foregoing, it would be of great commercial value to produce a treatment for snoring that overcomes the disadvantages described above, and to offer snorers a new, highly effective composition, tolerated by the body and specifically, the nasal mucus, which is capable of treating or preventing snoring.

In accordance with the present invention, the new nasal solution comprises natural or semi-synthetic polymers of a high molecular weight such as mucopolyssacharides of the glycosaminoglycane type, which can be found either in their natural form, or which are synthesized xylanes that are extracted from certain types of wood, for example beech, and are then transformed by synthesis into sulfuric polyester sodium salt.

Thus, we can obtain pentosane polysulphate which is described in the French patent no. 1,050,576 dated Jun. 2, 1952 or the BS no. 2,227 dated Jul. 12, 1962.

Basically, these are analogous structures of natural sulphated mucopolysaccharide acids, such as sulfuric chondroitin acids, keratosulphates, dermatane sulphates, heparin, or other mucopolysaccharides such as hyaluronic acid. In each case, these are polyanions of a general type of structure:

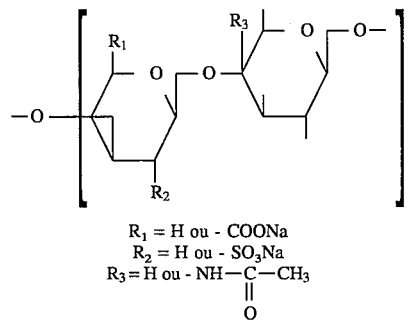

$R_1 = H$ ou - COONa
$R_2 = H$ ou - $SO_3Na$
$R_3 = H$ ou - NH—C—$CH_3$
              ‖
              O

These substances have properties which are sometimes comparable, but often vary one from the other. They are known under the class name of heparinoids, in spite of the fact that most of them, as is the case for chondroitin sulphate, or for pentosane polysulphate, no longer have an anti-clotting action which is characteristic of true heparin type substances as previously described. Thus, certain derivatives are used as anti-vital agents (Zbl. Bakt. Hyg. I Abt. Orig. 1977, A 237, pages 1–34), and others are used as fibrinolytic hypolipemiants as is the case for pentosane polysulphate (Arzneim. Forsch. 1972, 22, pages 759–763).

Others, such as chondroitin sulphate, have been described either as having properties which preserve the ocular tissues, or are able to play the role of a tear substituent (European patent no. 0063973). In the last case mentioned, certain fractions of chondroitin sulphate (type A) are used in preference to other fractions (B or C or mixtures of A+C).

These are always highly absorbent, high viscosity substances whose structure is often very similar to that of natural tissues such as cartilage, conjunctiva tissue, etc. For example, chondroitin sulphate A, instilled in the form of eye lotion at 3%, has revealed a major mucometic activity when applied to the rabbit eye, owing to its capacity of preserving the epithelial surface at the level of the microstructures (J. Fr. Ophtalmol. 1984, 1, pages 41–50).

The applicant has discovered that some polysacharides, whose molecular weight ranges between 1,000 and 1,000,000, are remarkably effective in their activity as far as the nose is concerned, and more especially in preventing snoring for a prolonged period of time. Most of these polyanionic substances described above have proved this. Polyanionic substances, such as heparin itself or heparinoids, may not be used to this end owing to the troublesome effects they have on the system itself. Thus, heparin has a major anti-clotting activity at the level of the nasal mucus or on the system, meaning that this substance can never be used in the new anti-snoring treatment.

On the other hand, applicant has learned that polysulphated derivatives of xylene, dextran, polyuronids or mucopolysaccharides, are well suited to treatment or prevention of snoring, given that they have no anti-clotting properties of their own. Moreover, they may also be applied in large doses without altering the nasal mucus and without causing systemic toxicity. In addition, it was discovered by accident that for some of the foregoing compounds, the nasal passages proved to be an excellent way in which to apply them; moreover, some of them even presented hypolipemiant properties.

Therefore, the applicant may well claim the discovery of new therapeutic indications, as well as a totally different method of presenting and applying the substances (nasal application) to those which have been previously advocated (i.e., capsules, injections, eye lotion).

In accordance with this invention, the new composition to prevent or treat snoring by means of nose drops applied in the form of solution, has as its main active constituent one of the mucopolysaccharides mentioned above, and more particularly, chondro it in sulphate sodium salt, whose molecular weight lies between 1,000 and 1,000,000.

The composition takes the form of a white powder obtained from fish or mammal cartilage. It has neither a smell nor a taste, and it does not decompose in water whose pH lies between 5 and 8 and in concentrations having a density is between 1 and 10%.

Apart from its above mentioned active constituents, and more precisely sodic chondroitin sulphate, the compositions for this nasal solution, must contain various formulating agents to enable them to be applied comfortably and easily to humans.

These constituents are essentially buffers, substances with isotonic properties and perfumes whose roles are well known. The choice of a preservative to be incorporated into the composition is a delicate one, given that the glycosaminoglycanes used in this invention are mainly polyanions which are negatively loaded, as previously indicated. Given that most of the antiseptics which can be used as preservatives are part of the chemical families which are positively loaded (as for example is the case of benzalkonium chloride, quaternary ammoniums in general, chlorohexidine salts, etc.), the choice of a nontoxic preservative which is well tolerated by the nasal mucus was in fact a delicate one. Thus, derivatives such as Imiduree and DMDM hydantoin might have been used in the final composition had their poor local tolerance not eliminated them from the list of available choices. The derivatives of p-hydroxybenzoic acid were not chosen either due to their allergising powers. The mercury derivatives, such as phenylmercury salts (nitrate, borate, acetate) were the only ones which presented the best safety/effectiveness ratio when they were used in very low concentrations (mg%).

Furthermore, when these water soluble mucopolysaccharide derivatives described above were combined with various substances of plant origin, we noticed that the clinical effectiveness of the final composition could be greatly increased. This is a particularly interesting case of a synergistic effect in the field of pharmaco-therapy.

These plant substances, among which we can list Belladonna, Sambucus and Bryonia, are they themselves synergised by various mineral constituents which are used in homeopathic concentrations. Preferably, the plant substances themselves may be diluted in to low concentrated forms, like those used in homeopathy "(CH, the preferred designation for Hahnemann centesimal [1/100] attenuations, which clearly indicates both the scale used and the method of attentuation [The Homeopathic Pharmocopela of the United States])".

The aqueous solutions well suited to nasal applications, may contain around 0.1% to 10% of their weight in soluble polysaccharide sodium salt, for example, pentosane sulphate, chondroitin sulphate and hyaluronic acid. It is recommended that these solutions be applied once before going to bed but they may be applied several times if required during the night.

The invention will no doubt be more easily understood from the description which follows, of which a part relates to a series of examples of nasal solutions, and another part concerns the clinical tests conducted using these compositions, or at least using one type of composition based on mucopolysaccharides chosen from the list which has been described above.

EXAMPLES OF COMPOSITIONS USED IN THE INVENTION

Example 1

| | |
|---|---|
| Pentosane sulphate sodium salt | 5.00 g |
| Sodium chloride | 0.37 g |
| Phosphate buffer (pH 7 +/− 0.5) | 0.35 g |
| Phenylmercury borate | 0.003 g |
| Purified water | 100 ml |

Example 2

| | |
|---|---|
| Hyaluronic acid sodium salt | 4.00 g |
| Boric acid | 1.200 g |
| Phosphate buffer (pH 7 +/− 0.5) | 0.35 g |
| Phenylmercury borate | 0.002 g |
| Purified water | 100 ml |

Example 3

| | |
|---|---|
| Chondroitin sulphate sodium salt | 3.00 g |
| Anhydrous monopotassic phosphate | 0.10 g |
| Anhydrous dipotassic phosphate | 0.25 g |
| Sodium chloride | 0.37 g |
| Phenylmercury nitrate | 0.002 g |
| Purified water | 100 ml |

Example 4

Identical to example 3, with the only exception that we add a homeopathic mineral and plant mixture made up of Alumina, Belladonna, Byrona, Plumbum and Sambucus at 5CH, and rose water at 5%.

Hence, it may be noted that aromas, buffers, products of plant origin and preservative antiseptics may be added to the main active agent of the composition.

Clinical Tests

Clinical tests were conducted to study the effectiveness of the nasal solution of the present invention, in reducing or eliminating snoring.

Eighty patients were chosen for clinical tests. The reason for choosing such a high number of patients may be justified by the fact that so many specialists have lost interest in the treatment of snoring. Indeed, due to the special nature of this ailment, whose treatment is aimed at eliminating a symptom which the patient himself does not complain of directly, given that the latter does not tend to think of himself as suffering from an illness in the traditional sense of the word.

In the selection of these volunteers, no criteria of age, sex or profession were used. All the volunteers had the following common characteristics:

1. Both themselves and their partners agreed that they snored in a sufficiently noisy way to disturb others during the night.
2. They did not suffer from rhinopharyngeal infections.
3. They did not have a displacement of the wall of the nasal fossae.
4. They slept regularly with the same partner, given that the latter is the only person who is able to help in assessing the effects of the treatment.

Obese people (that is those weighing over 100 kg) and who suffered from organic ailments such as a narrow pharynx were not selected for these tests.

The patients who were selected were not allowed to use another course of treatment against snoring other than this new nasal solution for the duration of these clinical tests. Patients who had already undergone previous courses of treatment with the same aim in mind were accepted.

The product which was tested is indicated in example 3.

Instructions For Use of This Product

This product was applied a few minutes before going to sleep. If sleep was interrupted, or if snoring started up again during the night, a second or even a third application was recommended.

The following instructions were provided with the samples that were handed out to the patients:

"In a lying down position on the back, instill a little solution into each nostril. Pinch the two nostrils together for approximately one minute to enable the product to remain in contact with the mucus for as long a period as possible".

The patients were then examined and were questioned: before the product was applied, —on each month after the beginning of the course of treatment, —three months after the beginning of the course of treatment.

At each examination, the patients were given enough samples of the solution to last until the following examination.

During the trial period, the clinical or functional tests gave rise to a certain number of questions to which the patients replied concerning snoring, whether it had:

—totally disappeared,

—disappeared for a given period, then had reappeared on a more or less regular basis, —never disappeared at all, but had become less regular and not as serious, —improved, before worsening again.

Results

Only a few files could be used after three months of treatment in comparison to the 80 patients selected. This result was expected given that a great number of patients did not return for follow-up.

The results were examined on 48 out of the 80 volunteers chosen.

The assessment of the effects of this treatment was left to the patients themselves, even if this meant a lowering of the final score. This approach enabled us to avoid overenthusiastic answers on the part of some patients.

The chart below gives an indication of the results obtained after three months of treatment using the new nasal solution.

| RESULTS OF THE THERAPY | NUMBER OF PATIENTS | PERCENTAGE OF PATIENTS |
| --- | --- | --- |
| Total Recovery | 9 | 19 |
| Improvement | 31 | 64 |
| Failure | 8 | 17 |

In the case of 9 patients, snoring was totally eliminated (19%) 6 patients out of the 9 were occasional snorers and 3 were regular snorers.

In 31 out of the 40 patients having completed the trial period, an obvious improvement in their symptoms was reported, either on information provided by their sleeping partners, or by the patients themselves when questioned.

Out of this percentage, there were those who noticed either that the intensity of the noise was reduced (21 patients), or that the noise emitted was different ("breathing sounds" rather than actual "snoring").

Questioning the patients did not enable us to determine whether the actual tone of snoring had been altered or if it was simply a question of the sound coming from another place (for instance, sibilant sounds in the case of those suffering from pneumonitis).

It should be pointed out that out of these 31 patients who had improved due to the treatment, 10 were reported to have been totally cured for a period of time, before the snoring symptoms returned (33% of the patients).

Total failure was noticed on the part of 8 patients who completed the course of treatment, that is 17% of the sample population of patients on whom the effectiveness of the product was assessed. In certain cases, the improvement was only temporary, however, on the whole the sleeping partners of those questioned reported that the symptoms had persisted.

In 4 cases, there was no improvement in snoring, in some cases the symptoms had even become progressively worse.

This product was well tolerated in all the cases reported above. Moreover, it should be pointed out that certain patients reported signs of beneficial effects which had not been expected in the context of this clinical test, such as:

—better conjugal or family relationships,

—a better night's sleep (a great number of patients said that they "slept better" even if they had to reapply the solution during the night), —the disappearance of or a reduction in drowsiness during the day, which should be perhaps examined in the context of the previous remark, —an improvement in breathing before going off to sleep. This remark is perhaps only another way of expressing a lessening of or the disappearance of snoring.

This clinical test carried out on 48 patients who were re-examined after the three months of treatment, has enabled us to estimate the effectiveness of the present nasal solution in the symptomatic treatment of snoring.

83% of the patients (and/or their partners) who were questioned reported either a recovery (19%) or a major improvement as far as the symptoms were concerned (64%).

17% of the people examined did not respond to the treatment. The ineffective nature of the treatment is probably directly linked to more chronic cases of snoring which require surgery. Yet in each case examined, there were no problems of local intolerance to the treatment.

That which is claimed is:

1. A method of treating nonsurgery-requiring chronic snoring comprising the administration to the snorer's nasopharyngeal mucous membranes shortly prior to the snorer's retiring to sleep, of an effective amount of an aqueous buffered nasal solution consisting essentially of chrondroitin sulphate sodium salt at a concentration of from 0.1 to 10 weight percent, based on the total weight of the nasal solution.

2. The method according to claim 1, wherein the chondroitin sulphate sodium salt has a molecular weight of from 1,000 to 1,000,000.

3. The method according to claim 1, wherein the nasal solution contains a phenylmercury salt as a preservative therefor.

4. The method according to claim 3, wherein the phenylmercury salt is selected from the group consisting of phenylmercury nitrate, phenylmercury borate and phenylmercury acetate.

5. A method of treating snoring comprising the administration to the snorer's nasopharyngeal mucous membranes, shortly prior to the snorer's retiring to sleep, of an effective amount of a nasal solution consisting essentially of an aqueous solution of from 0.1 to 10 percent by weight of chondroitin sulfate sodium salt based on the total weight of the nasal solution and a homeopathic component selected from the group consisting of allophathic plants, homeopathic plants and minerals.

6. The method according to claim 5, wherein the homeopathic component is a therapeutically effective amount of a component selected from a group consisting of Belladonna, Bryonia, Sambucus, Alumina, Plumbum, and a mixture thereof, wherein the component is present in the aqueous solution in a Hahnemanian dilution.

7. The method according to claim 6, wherein the plant component is present in a concentration of from 1 CH to 100 CH.

8. A method of treating snoring comprising the administration to the snorer's nasopharyngeal mucous membranes, shortly prior to the snorer's retiring to sleep, of an effective amount of a nasal solution consisting essentially of an aqueous solution of (i) from 0.1 to 10 percent by weight of chondroitin sulphate sodium salt based on the total weight of the nasal solution, (ii) sodium chloride, (iii) a phenylmercury salt, and (iv) a phosphate buffer.

9. A method of treating snoring comprising the administration to the snorer's nasopharyngeal mucous membranes, shortly prior to the snorer's retiring to sleep of an effective amount of a nasal solution consisting essentially of an aqueous solution of from 0.1 to 10 percent by weight of chondroitin sulphate sodium salt based on the total weight of the nasal solution, sodium chloride, a phenylmercury salt, a phosphate buffer and a homeopathic mineral and plant mixture containing Alumina, Belladonna, Plumbum and Sambucus, the mixture being present in a concentration of 5 CH.

10. The method according to claim 9, wherein the nasal solution contains rosewater.

* * * * *